United States Patent [19]

Ekholm

[11] Patent Number: 4,523,581

[45] Date of Patent: Jun. 18, 1985

[54] CHIROPRACTIC TABLE CUSHION DROP RELEASE MECHANISM

[75] Inventor: Carl R. Ekholm, Elgin, Ill.

[73] Assignee: Standex International Corporation, Salem, N.H.

[21] Appl. No.: 541,364

[22] Filed: Oct. 12, 1983

[51] Int. Cl.$^3$ .............................................. A61F 5/00

[52] U.S. Cl. ...................................... 128/70; 269/323; 128/68

[58] Field of Search ..................... 128/68, 68.1, 70–74; 124/41 R; 269/322, 323, 324

[56] References Cited

U.S. PATENT DOCUMENTS

| | | | |
|---|---|---|---|
| 2,715,557 | 8/1955 | Rock | 128/70 |
| 3,092,102 | 6/1963 | Thompson | 128/70 |
| 3,968,784 | 7/1976 | Miller | 124/41 R |
| 4,050,454 | 9/1977 | Ekholm | 128/70 |

*Primary Examiner*—Richard J. Apley
*Assistant Examiner*—Robert Bahr
*Attorney, Agent, or Firm*—Mason, Kolehmainen, Rathburn & Wyss

[57] ABSTRACT

A chiropractic table cushion drop release mechanism wherein a latch member which is spring biased into engagement with a detent mechanism to hold the cushion in an elevated position is restrained from inward movement after it has released the detent so that the frictional drag of the spring biased latch is removed and the cushion can drop freely to a desired lower position.

8 Claims, 5 Drawing Figures

CHIROPRACTIC TABLE CUSHION DROP RELEASE MECHANISM

The present invention relates to chiropractic tables and, more particularly, the chiropractic tables of the type shown in U.S. Pat. Nos. 3,092,102 and 3,343,531 in which individual cushion sections of the table may be held in an upper position by a spring biased detent arrangement which releases when force is applied to the portion of the body lying on the elevated cushion so that the cushion is moved downwardly to a lower position.

While chiropractic tables of the above described type have been quite successful, they suffer from the disadvantage that a substantial drag is produced by the detent mechanism after the cushion had been released with the result that the cushion drop to the lower position is relatively slow, which is relatively more traumatic for the patient, and requires more work on the part of the doctor. Furthermore, the latch member employed in the detent mechanism of U.S. Pat. No. 3,092,012 is expensive to manufacture and it is difficult to maintain reliability and uniformity of adjustment due to the manner in which the latch is pivotally mounted.

It is an object of the present invention to provide a new and improved cushion drop release mechanism for a chiropractic table wherein one or more of the above discussed disadvantages of the prior art arrangements is eliminated.

It is another object of the present invention to provide a new and improved cushion drop release mechanism for a chiropractic table wherein the cushion may quickly drop to a desired lower position when the detent mechanism which holds the cushion in an elevated position is released.

It is a further object of the present invention to provide a new and improved cushion drop release mechanism for a chiropractic table which is free from frictional drag after the detent mechanism is released so that the cushion may freely drop to a desired lower position.

It is a still further object of the present invention to provide a new and improved cushion drop release mechanism for a chiropractic table wherein a latch member is spring biased into engagement with a detent mechanism to hold the cushion in an elevated position and means are provided for restraining the latch member from inward movement after it has released the detent so that the frictional drag of the spring biased latch is removed and the cushion can drop freely to a desired lower position.

It is another object of the present invention to provide a new and improved cushion drop mechanism for a chiropractic table which employs an improved latch member which is of simplified construction and is economical to manufacture on a mass production basis.

The invention both as to its organization and method of operation, together with further objects and advantages thereof, will best be understood by reference to the following specification taken in connection with the accompanying drawings, in which.

Figures 1, 2, 3:
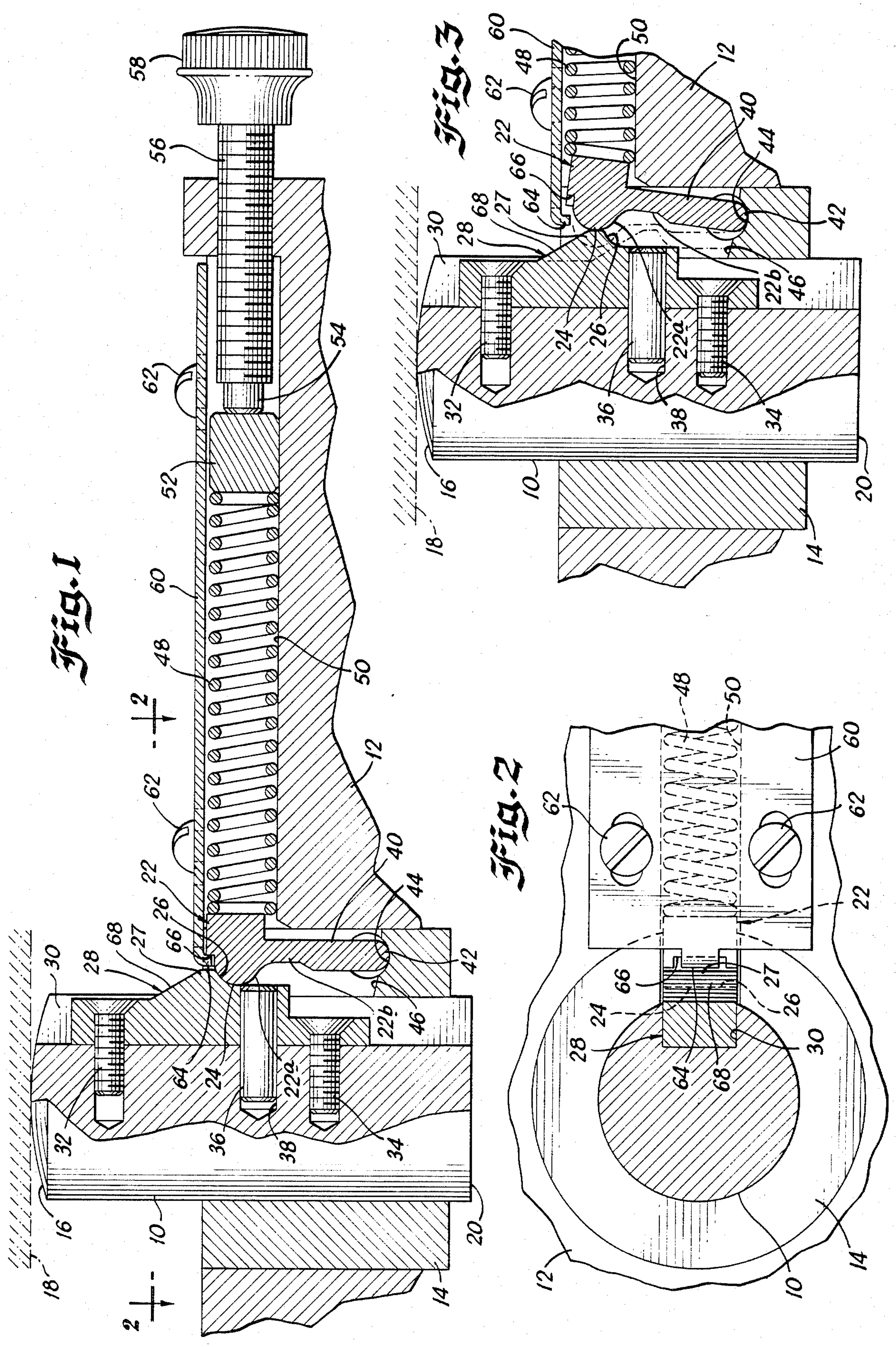
FIG. 1 is a sectional side elevation view of a pelvic cushion drop release mechanism embodying the features of the present invention.
FIG. 2 is a sectional view taken along the line 2—2 of FIG. 1.
FIG. 3 is a view similar to FIG. 1 but showing the latch in a released position.

Referring now to the drawings, the present invention is therein illustrated in conjunction with a pelvic cushion drop release mechanism wherein a post 10 is mounted for vertical movement within a housing 12 and is positioned for sliding movement within a bronze bushing 14 which is mounted in the housing 12. The post 10 is provided with a curved top surface 16 which engages and supports one end of a pelvic cushion indicated generally at 18, the other end of this cushion being pivotally mounted in a conventional manner on the frame of the chiropractic table.

Before a chiropractic adjustment is made on a patient lying on the pelvic cushion 18, the post 10 is raised to the elevated position shown in FIG. 1 by any suitable means such as by manual adjustment of a member in engagement with the bottom surface 20 of the post 10, or by suitable pneumatic actuating means.

When the post 10 is raised to the elevated position shown in FIG. 1 it is held in this position by means of a latch member indicated generally at 22 which is provided with a rounded head portion 24 which is positioned beneath a complimentary surface 26 on a key 28 which is secured to the post 10. More particularly, post 10 is provided with a keyway 30 within which the key 28 is secured by means of the screws 32 and 34. In order to maintain accurately the height to which the post 10 is raised when in the elevated position, the key 28 is also located relative to the post 10 by means of a dowel pin 36 which extends through the key 28 and into an opening 38 in the post 10. The latch member 22 is provided with a shank portion 40 having a rounded end 42 which is positioned in a transverse groove 44 formed in the milled out surface 46 of the bushing 14. A coil spring 48 is positioned within a groove 50 formed in the top surface of the housing 12, one end of the spring 48 engaging the head portion of the latch 22 and the other end thereof engaging a pusher block 52 which is positioned in the groove 50 between the spring 48 and the end 54 of an adjustment screw 56 to which is connected an adjustment knob 58. By adjustment of the knob 58 the force with which the latch 22 is held in engagement with the key 28 may be varied so as to vary the amount of pressure which must be exerted through the cushion 18 before the detent mechanism releases. Such variation of pressure is necessary to accommodate patients of various weights and anatomical builds from children to obese adults. More particularly, when a predetermined amount of force is exerted in the pelvic area of the patient so as to produce a predetermined downward force on the upper end 16 of the post 10 the latch member 22 is pivoted outwardly against the force of the spring 48 so as to permit the cushion 18 and post 10 to move downwardly to a predetermined lower position, preferably in the order of ½" below the elevated position in which the post 10 is held by the above described detent mechanism.

In accordance with an important aspect of the present invention a cover plate 60, which is provided to retain the spring 48 and the block 52 within the groove 50 and is secured to the housing 12 by means of the screws 62, is provided with a downturned lug portion 64 which engages a shoulder 66 formed in the latch member 22 so as to restrain the latch member 22 from movement toward the axis of the post 10. In addition, the projecting nose portion 27 of the key 28 is provided with a sloping upper edge 68 to provide clearance between the key 28 and the head portion of the latch member 22 after the projecting portion 27 has forced the latch member 22 inwardly against the bias of the spring 48 to release the detent mechanism. As a result, once the detent mechanism releases, the post 10 and cushion 18 can drop freely to the lower position without any frictional drag, such as produced in the prior art arrangement shown in Thompson U.S. Pat. No. 3,092,102, for example. As the post 10 and cushion 18 are reset to their initial elevated position the sloping portions 68 of the key 28 engages the head portion *22a* of the latch member 22 and pivots the latch member 22 against the force of the spring 48 to a point at which the projection 27 can move upwardly above the head portion *22a* and be seated on the upper curved surface of the head portion *22a*, as shown in FIG. 1. It will also be noted that the latch member *22a* is provided with an undercut portion *22b* immediately below the head portion *22a* so as to provide clearance for the projecting portion 27 of the key 28 as the latch member 22 is restrained by the stop means 64 and the post 10 falls to its lower position. It will also be noted that the rounded bottom end portion 42 of the latch member 22 is free to pivot within the groove 44 formed in the bushing 14 so that the latch member 22 is free to rock during the detent release action but remains essentially centered within the groove 44 so that reliable and uniform detent release action is provided for a particular setting of the adjustment knob 58. The key 28 is preferably of 4140 steel hardened to 50/60 Rc. and the latch member 22 can either be made of steel, such as cold rolled steel No. 1018 or, in the alternative, may be made of a powdered metal which is molded in the appropriate shape and is of sufficient hardness to provide good wearing qualities and reduced coefficient of friction for freedom of movement in its contact with the key 28. The powdered metal construction is preferred as a low cost construction to eliminate the machining necessary when the latch member 22 is made of steel.

While the arrangement of the present invention has been illustrated in FIGS. 1 to 4 in connection with a cushion drop release mechanism for a pelvic cushion, it will be understood that a similar arrangement may be used for the dorsal, lumbar or other cushions or sections of a chiropractic table in an arrangement similar to that disclosed in Thompson patent No. 3,092,102 wherein a cam member is employed in place of the adjustment knob 58 to vary the relative forces exerted on the dorsal and lumbar cushions, adjustable members being placed in the groove 50 between the springs of the dorsal and lumbar sections to provide adjustment of individual release pressures for each cushion, as discussed in Thompson U.S. Pat. No. 3,092,102.

Figures 4, 5:
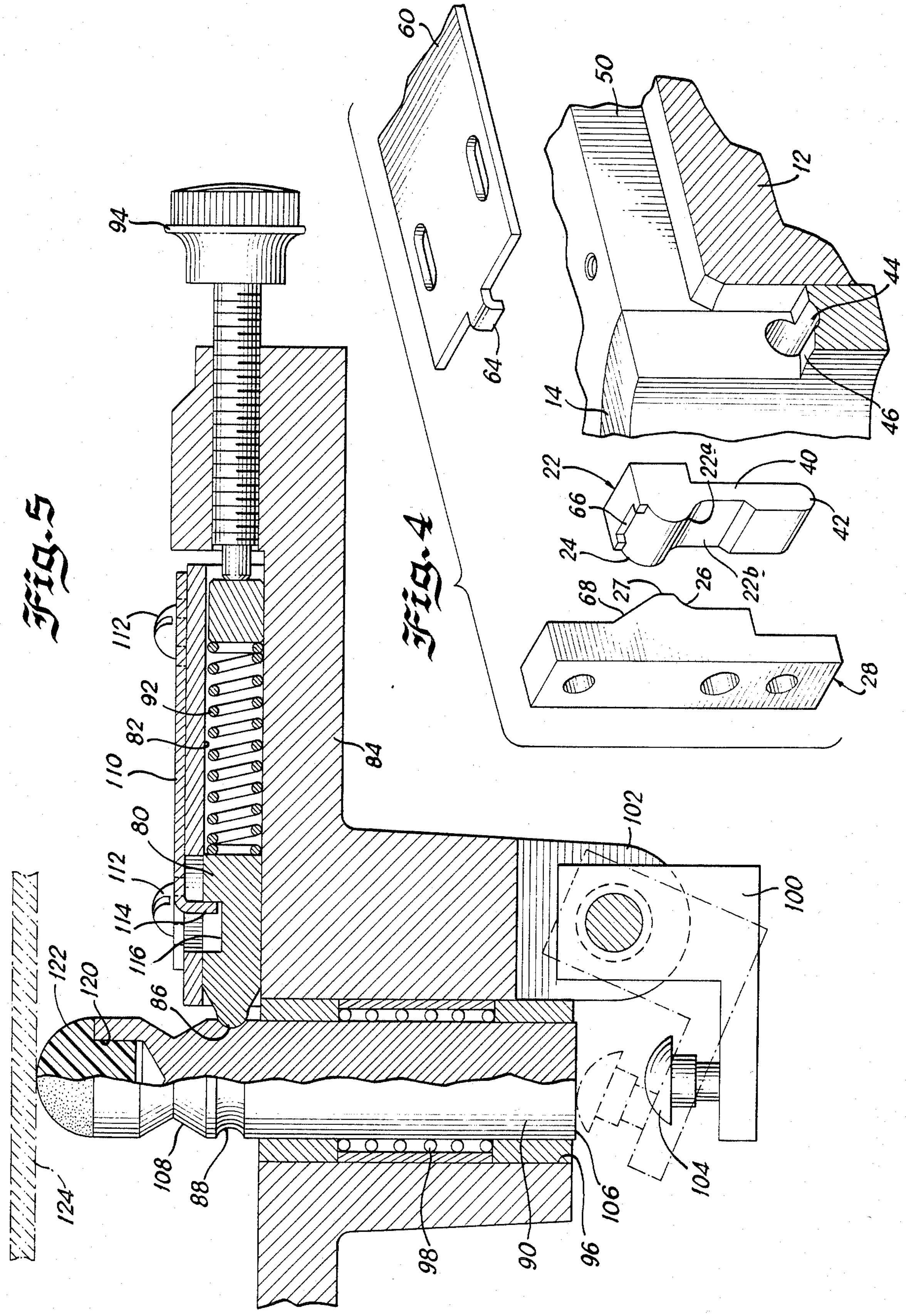
FIG. 4 is an exploded perspective view of the arrangement of FIG. 1.
FIG. 5 is a sectional side elevation view of an alternative embodiment of the present invention.

The free drop cushion release mechanism of the present invention may also be employed in connection with the head rest cushion structure of the chiropractic table as shown in FIG. 5 of the drawings. Referring to this figure, the latch member 80 which is mounted within a groove 82 formed in the housing 84, has a detent nose portion 86 formed in the forward end thereof which is normally forced into engagement with the groove 88 formed in the upper end of the post 90, the pin 86 being forced into the groove 88 by means of the spring 92 the tension of which is adjustable by means of the knob 94. The post 90 is mounted within the bore 96 in the housing 84 by means of the low friction ball bushing 98 and may be elevated to the detent position by means of the lever 100 which is pivotally mounted in the downwardly projecting lug portion 102 of the housing 84 and is provided with a round headed stud 104 in the outer end thereof which is adapted to engage the bottom end 106 of the post 90.

In accordance with the present invention, the post 90 is provided with an inwardly sloping surface 108 above the groove 88. The cover member 110, which is held in place by the screws 112, is provided with a downturned lug portion 114 which acts as a stop mechanism and engages the rear end of a recess 116 formed in the top wall of the latch member 80 so as to prevent inward movement of the latch member 80 after the pin 86 has been moved outwardly against the force of the spring 92 to clear the groove 88 and permit the post 90 to fall freely to a desired lower position. Preferably, the upper end of the post 90 is provided with a top opening recess 120 which is adapted to receive the lower end of a high density polyethylene spherical button 122 on which the mounting plate 124 of the head cushion of the chiropractic table (not shown) rests.

In operation, when a sufficient force is exerted on the upper end of the post 90 the nose 86 is moved out of the groove 88 against the force of the spring 92 and the post moves downwardly to the desired lower position. During such movement the latch member 80 is restrained by the stop lug 114 so that the nose 86 does not engage the inwardly sloping conical portion 108 of the post 90 and thereby permits a free drop of the head cushion to the desired lower position. The post 90 may then be actuated to the elevated position shown in FIG. 5 by actuation of the lever 100 by any suitable means.

While there have been illustrated and described various embodiments of the present invention, it will be apparent that various changes and modifications thereof will occur to those skilled in the art. It is intended in the appended claims to cover all such changes and modifications as fall within the true spirit and scope of the present invention.

What is claimed as new and desired to be secured by Letters Patent of the United States is:

1. An adjustable support mechanism for a chiropractic table cushion comprising a support, a post mounted in said support for movement in a vertical axis, a cushion supported at least in part on the upper end of said post, a latch means mounted in said support for movement toward and away from said axis, said post having detent means cooperating with said latch means for holding said cushion in an elevated position, said detent means comprising a shoulder portion adapted to be seated on said latch means and an inwardly recessed portion above said shoulder portion, adjustable spring means for urging said latch means into engagement with said shoulder portion of said detent means so that a predetermined downward force on said cushion is required to release said detent means from said latch means and permit said cushion to drop from said elevated position, and stop means for limiting movement of said latch means toward said axis as said latch means moves into said recessed portion of said detent means, said stop means being effective to prevent said latch means from engaging said post as said latch means moves into said recessed portion after release of said detent means so that said cushion can freely drop to a desired lower position.

2. A support mechanism as set forth in claim 1, which includes means defining a channel within which said latch means is movably mounted, and a cover plate for said channel, said stop means comprising a downturned lug portion on said cover plate which is adapted to engage said latch means and restrain the same against inward movement.

3. A support mechanism as set forth in claim 1, wherein said post is provided with a vertically extending slot and said detent means comprises a key mounted in said slot and having a portion projecting outwardly beyond the periphery of said post, said projecting portion being adapted to be seated on said latch means to hold said cushion in said elevated position said key having an inwardly and upwardly and inclined portion above said projecting portion to provide said inwardly recessed portion of said detent means.

4. A support mechanism as set forth in claim 3, wherein said latch means comprises a member mounted on said support for pivotal movement about a point below said projecting portion of said key and having a head portion urged into engagement with said projecting portion by said spring means to hold said cushion in said elevated position.

5. A support mechanism as set forth in claim 4, which includes means defining a channel in said support in which said spring means and said head portion of said latch means are positioned, and a cover plate for said channel, said stop means comprising a downturned lug portion on said cover plate which is adapted to engage said head portion and restrain said member from engaging said post as said cushion drops to said desired lower position.

6. A support mechanism as set forth in claim 4, wherein said head portion of said member is made of hardened powdered metal.

7. A support mechanism as set forth in claim 3, which includes a dowel pin extending transversely through said key and into said post so that said key remains accurately located relative to said post and retains said cushion at said elevated position over long periods of usage.

8. A support mechanism as set forth in claim 4, which includes a bushing mounted in said support, said post being slidably mounted in said bushing for movement along said vertical axis, and means defining a recess in said bushing adapted to receive the bottom end of said member, said bottom end being free to rock within said recess so that said member remains centered in said recess.

* * * * *